US010596371B1

(12) United States Patent
Lisy et al.

(10) Patent No.: US 10,596,371 B1
(45) Date of Patent: Mar. 24, 2020

(54) GALVANIC VESTIBULAR STIMULATION (GVS) SYSTEMS, DEVICES AND METHODS

(71) Applicants: Frederick J. Lisy, Euclid, OH (US); Anthony Opperman, Wickliffe, OH (US); Matthew D. Tarler, Avon, OH (US); Angela Lisy, Euclid, OH (US); Vincent R. Cozza, Potomac, MD (US)

(72) Inventors: Frederick J. Lisy, Euclid, OH (US); Anthony Opperman, Wickliffe, OH (US); Matthew D. Tarler, Avon, OH (US); Angela Lisy, Euclid, OH (US); Vincent R. Cozza, Potomac, MD (US)

(73) Assignee: Orbital Research Inc., Cleveland, OH (US)

( * ) Notice: Subject to any disclaimer, the term of this patent is extended or adjusted under 35 U.S.C. 154(b) by 195 days.

(21) Appl. No.: 15/491,322

(22) Filed: Apr. 19, 2017

Related U.S. Application Data

(60) Provisional application No. 62/324,560, filed on Apr. 19, 2016.

(51) Int. Cl.
    *A61N 1/36*     (2006.01)
    *A61N 1/04*     (2006.01)

(52) U.S. Cl.
    CPC ....... *A61N 1/36014* (2013.01); *A61N 1/0472* (2013.01); *A61N 1/36032* (2013.01)

(58) Field of Classification Search
None
See application file for complete search history.

(56) References Cited

U.S. PATENT DOCUMENTS

| | | | | |
|---|---|---|---|---|
| 5,762,612 A | * | 6/1998 | Campbell | A61N 1/20 600/558 |
| 6,496,712 B1 | * | 12/2002 | Dahl | A61B 5/042 600/374 |
| 6,785,569 B2 | * | 8/2004 | Schmidt | A61B 5/04025 600/372 |
| 2009/0023554 A1 | * | 1/2009 | Shim | A63B 22/02 482/4 |
| 2010/0004715 A1 | * | 1/2010 | Fahey | A61H 39/002 607/48 |
| 2010/0268302 A1 | * | 10/2010 | Botros | A61N 1/36032 607/57 |
| 2010/0304864 A1 | * | 12/2010 | Johnson | A61B 5/0402 463/36 |
| 2016/0045733 A1 | * | 2/2016 | McGeoch | A61B 5/0531 607/60 |

* cited by examiner

*Primary Examiner* — Erica S Lee
(74) *Attorney, Agent, or Firm* — Brian Kolkowski

(57) ABSTRACT

The present invention is directed to systems, devices and methods for stimulating perceived motion, and more particularly to stimulating perceived motion in three axes. The invention is further directed to stimulating such perceived motion when accompanied by visual stimuli. The invention is further directed to utilizing as few as two distinct pairs of electrodes to administer electrical stimulation to generate the perceived motion. The invention is further directed to systems, devices and methods to minimize side effects while utilizing electrical currents create the perceived motion.

20 Claims, 5 Drawing Sheets

GALVANIC VESTIBULAR STIMULATION (GVS) SYSTEMS, DEVICES AND METHODS

CROSS REFERENCE TO RELATED APPLICATIONS

This application is a nonprovisional application that claims the benefit of U.S. Patent application Ser. No. 62/324,560, filed on Apr. 19, 2016.

BACKGROUND OF THE INVENTION

1. Field of the Invention

The present invention is directed to systems, devices and methods for stimulating perceived motion, and more particularly to stimulating perceived motion in three axes. The invention is further directed to stimulating such perceived motion when accompanied by visual stimuli. The invention is further directed to utilizing as few as two distinct pairs of electrodes to administer electrical stimulation to generate the perceived motion. The invention is further directed to systems, devices and methods to minimize side effects while utilizing electrical currents create the perceived motion.

2. Technical Background

Emerging markets are presently ripe for enhanced virtual experience and/or augmentation of real experience. Examples of such markets include entertainment industries such as movies and film, video gaming, television, and other interactive media, as well as other industries such as medical, military and commercial uses. Stimulation of perceived motion, particularly when accompanied by visual stimuli, can enhance a user's experience in these and other markets and industries by mimicking and/or augmenting real-life sensations of movement in a subject to simulate or enhance the intended movement or motion.

Galvanic vestibular stimulation (GVS) is the process of sending specific electric messages to a nerve in the ear that maintains balance. There are two main groups of receptors in the vestibular system: 1) the three semi-circular canals; and 2) the two otolith organs (the utricle and the saccule)". GVS technology has been used in a single-channel configuration for quite some time, but such single-channel systems are limited in the amount and type of stimulation, and thus perceived motion, they can provide. Multi-channel, multi-axial configurations have been the subject of more recent development efforts, but have numerous drawbacks in their current state, particularly requiring unwieldy and uncomfortable electrode configurations as well as being complicated and not user-friendly. Of particular note is the fact that current GVS technology typically requires at least one electrode to be placed on the back of a subject's head or neck, which can be greatly inhibited by the presence of hair on many subjects.

Further, GVS systems and methods typically cause one or more side effects related to the provision of electrical current through electrodes in contact with the subject's skin. Dermal effects, which are sensations on the subject's skin such as burning, prickling, cooling, tapping, or the like, may occur at or near electrode sites. Flashing lights or other visual effects may occur as a result of the electrical current passing through or near the optical nerve. Subjects may also experience perceived tastes such as iron, metallic or other such tastes. These side effects may be real or merely perceived, that is, felt but not actually occurring. For example, a subject may experience a warming or burning sensation on his or her skin where the electrode is in contact with the skin, but the skin is not actually increasing in temperature or burning. The sensation may be a result of the excitation of nerve endings by the electrical stimulation, but may or may not be accompanied by an actual increase in temperature or burning of the skin. Whether real or perceived, these side effects may cause discomfort and lack of enjoyment or performance.

It is therefore an object of the present invention to provide GVS systems, devices and methods that provide multi-channel, multi-axial perceived motion. It is another object of the present invention to provide such perceived motion while minimizing the number of electrodes required and the number of channels of stimulation required. It is still further an object of the present invention to provide such stimulation while maximizing the comfort and ease of use for the user, including electrode placement that is easy and preferably not require alteration of a subject's body (e.g., removal of hair), and further to minimize side effects of electrical stimulation. It is yet further an object of the present invention to combine GVS with other forms of stimulation, such as visual stimuli, to minimize the electrode stimulation required and overall complexity of the systems and methods while also maximizing the amount of perceived motion stimulated and thus the user's overall experience.

SUMMARY OF THE INVENTION

The present invention is directed to systems, devices and methods for stimulating perceived motion, and more particularly to stimulating perceived motion in three axes. The invention is further directed to stimulating such perceived motion when accompanied by visual stimuli. The invention is further directed to utilizing as few as two distinct pairs of electrodes to administer electrical stimulation to generate the perceived motion. The systems, devices and methods of the present invention are further preferably useful or adaptable for other applications including transcranial direct current stimulation (tDCS) and the diagnosis of mTBI.

Generally, GVS is performed by providing pairs of electrodes, strategically placed on a subject's body. In each pair of electrodes, typically one electrode is used to provide or inject an electrical stimulus into the subject and the second electrode provides an exit pathway allowing the injected current to leave the subject's body. The target and/or desired stimulation pattern for the electrical stimulus is generally the determining factor when deciding electrode placement. Depending on the number of electrodes used, many possible stimulation patterns of electrical current pathways may be conceived. Preferably, 10 or fewer electrodes are used. More preferably, 9 or fewer electrodes are used. Yet more preferably, 8 or fewer electrodes are used. Still more preferably, 7 or fewer electrodes are used. Even more preferably, 6 or fewer electrodes are used. Still yet more preferably, 5 or fewer electrodes are used. Yet even more preferably, 4 or fewer electrodes are used. Some embodiments may utilize fewer than 4 electrodes, such as 3 or 2 electrodes, depending on the type and number of axes of perceived motion that are desired for a particular application; however, at least four electrodes are preferably used to stimulate three axes of perceived motion. Electrodes for GVS can be placed in numerous locations on the subject, preferably on his or her head, including, but not limited to the forehead, back of the head and/or neck, high and/or low mastoid, earlobes, and the like. In one preferred embodiment of the present invention, four electrodes are utilized and placed in a pattern with one electrode on each of the subject's left and right earlobes, and two electrodes on the subject's forehead, preferably on each of the left and right sides thereof.

Once the electrodes are placed on the subject in their desired locations, they can be used to provide electrical stimulation any pattern whereby electrical current is delivered from one electrode to another. Electrical current can be passed between any two electrodes attached to the subject in order to stimulate a perceived motion associated with the particular electrical pathway and brain structure through which the electrical current is passed. An electrical current may be passed between electrodes to stimulate perceived roll motion (rotation in the coronal or frontal plane), perceived pitch motion (rotation in the sagittal or anteroposterior plane), and/or yaw motion (rotation in the vertical or transverse or axial plane). As such, this one preferred electrode configuration can be used to stimulate the three major directions of perceived motion for the subject. Electrical current may be driven to each of the electrodes individually or in combinations of electrodes. Preferably, in embodiments with two electrodes placed on a subject's forehead, electrical current is driven to each forehead electrode independently in order to steer the provided electrical current away from the optical nerve. In many embodiments, the same electrodes may be used to both provide electrical stimulation to the subject as well as to acquire physiological and electrophysiological signals from the subject. More preferably, the same electrodes may acquire physiological or electrophysiological signals from the subject simultaneously with providing electrical stimulation to the subject. Such electrodes shall be referred to as "dual-mode" electrodes within the scope of the present invention. As few as two electrodes may be used for various embodiments of this invention to provide stimulation to a subject.

Visual media, such as a video, can be used to augment the perceived motion. The visual stimulus provides a frame of reference and expectation of movement for the subject such that when combined with the GVS, allows the subject to actual feel or perceive as though he or she is experiencing the motion indicated by the visual stimuli and augment the perceived motion generated by the electrical stimuli.

Preferably the systems, devices and methods of the present invention operate in real-time. Real-time, in regards to the present invention preferably refers to the amount of time it takes for the system to receive inputs, such as from sensors measuring various attributes of the subject and/or any manual input, process the inputs and data, calculate or develop a GVS protocol or stimulation protocol, and to provide electrical stimulation to the subject to elicit the desired perceived motion. This entire process can be referred to as the GVS cycle. By real-time operation of the GVS cycle, preferably the GVS cycle requires 5 minutes or less from input to providing stimulation. More preferably, the GVS cycle requires 3 minutes or less from input to providing stimulation. Yet more preferably, the GVS cycle requires 1 minute or less from input to providing stimulation. Still more preferably, the GVS cycle requires 45 seconds or less from input to providing stimulation. Even more preferably, the GVS cycle requires 30 seconds or less from input to providing stimulation. Still yet more preferably, the GVS cycle requires 15 seconds or less from input to providing stimulation. Yet even more preferably, the GVS cycle requires 5 seconds or less from input to providing stimulation. Even still more preferably, the GVS cycle requires 1 second or less from input to providing stimulation. Yet still more preferably, the GVS cycle requires 750 microseconds or less from input to providing stimulation. Still even more preferably, the GVS cycle requires 500 microseconds or less from input to providing stimulation. Even yet more preferably, the GVS cycle requires 250 microseconds or less from input to providing stimulation. Still yet even more preferably, the GVS cycle requires 1000 nanoseconds or less from input to providing stimulation. Yet even still more preferably, the GVS cycle requires 500 nanoseconds or less from input to providing stimulation. Even still yet more preferably, the GVS cycle requires 100 nanoseconds or less from input to providing stimulation. Most preferably, the GVS cycle, from input to providing stimulation, is carried out substantially instantaneously.

The embodiments of the present invention are also envisioned as a tool to quantitatively diagnose mild traumatic brain injuries (mTBI). The system, devices and methods described herein can become a vestibular and ocular motor evaluation device that uses galvanic vestibular stimulation (GVS) and signal acquisition in hostile/noisy environments with minimal preparation. Minute pulses of electric stimuli (1 mv-3 mv) will be applied to specific areas on the head and neck to accurately and objectively detect even the most subtle of vestibular, postural, and ocular deficits associated with blast exposure and other mTBI. The embodiment will feature the electrodes to stimulate the vestibular system and induce postural instability. The device will then measure the degree of sway and time or latent response of postural recovery as compared to the subject's pre-recorded measurements via a three-axis accelerometer. These same electrodes will also be used to quantitatively measure saccadic and vestibulo-ocular reflex dysfunction via EOG (Electrooculography) signals collected from electrodes positioned on or near the extraocular muscles. This embodiment will provide medical personnel a means to quantify the latencies and frequency rates of specific ocular movements such as blink metrics and saccades as cognitive indicators of early signs of brain trauma. This innovation will also quantify the recovery rates of induced postural instabilities to accurately and acutely determine the level and nature of the TBI following a blast or impact head injury. This embodiment is envisioned as a means for corpsmen to identify those service members with vestibular and ocular concussive impairments, so that immediate action can be taken since these particular types of brain injuries take much longer to recover from (a few months) as compared to a typical three week concussion recovery period. Delaying a service member's return to duty will drastically reduce the number of cumulative injuries since vestibular symptoms often compromise a soldier's situational awareness and impair his reaction time to environmental stimuli. This embodiment will produce a quantified concussive profile that is impossible to acquire from the subjective balance and cognitive assessment tools (MACE and ANAM) currently being used in U.S. military deployment situations. Postural stability has been proven to be an objective measure in the assessment of mild head injuries. (Guskiewicz K M, Perrin D H, Gansneder B M. Effect of mild head injury on postural stability in athletes. J Athl Train. 1996; 31:300-306) and the results from a Hoffer et al. study objectively verified that vestibular impairments are common following blast exposure. (Hoffer M E, Balaban C, Gottshall K, Balough B J, Maddox M R, Penta J R. Blast exposure: vestibular consequences and associated characteristics. Otol Neurotol. 2010; 31(2): 232-36). Research done by Heitger and associates indicated that mTBI impairs the complex cerebral networks involved in ocular motor control. Heitger's work even suggests that assessment of eye movement function after mTBI can be a very effective tool in predicting adverse outcome in the form of post concussive syndrome (PCS) (Heitger M H, Jones R D, Anderson T J, A new approach to predicting post concussion syndrome after mild traumatic brain injury based upon eye movement function, EMBS 2008. 30th Annual International Conference of the IEEE). Additional features and advantages of the invention will be set forth in the detailed description which follows, and in part will be readily apparent to those skilled in the art from that description or recognized by practicing the invention as described herein, including the detailed description which follows, the claims, as well as the appended drawings.

One embodiment of the present invention includes a method of providing galvanic vestibular stimulation (GVS) to a subject to provide perceived motion, the method comprising steps of: providing to the subject a GVS system comprising a human interface device (HID), a central control device (CCD) and a current application device (CAD), the HID comprising at least four electrodes, each electrode comprising an upper surface and a lower surface with a plurality of surface features disposed on the lower surface, the CCD comprising a processor comprising at least one algorithm, and the CAD comprising a processor and an electrical current generator; integrating and synchronizing, with the CCD processor and at least one algorithm, input data to generate a GVS profile, translating the GVS profile, with the CAD processor into a current application profile; generating with the CAD electrical current generator a stimulation current according to the determined current application profile; and providing the generated stimulation current to the subject with at least two of the electrodes to provide a perceived motion to the subject in at least one dimension or direction.

Another embodiment of the present invention includes a method of providing galvanic vestibular stimulation (GVS) to a subject to provide perceived motion, the method comprising steps of: providing to the subject a GVS system comprising a human interface device (HID), a central control device (CCD) and a current application device (CAD), the HID comprising a modified eyewear or eyeglasses apparatus with at least two forehead electrodes and at least two ear electrodes, each electrode comprising an upper surface and a lower surface with a plurality of surface features disposed on the lower surface, the CCD comprising a processor comprising at least one algorithm, and the CAD comprising a processor and an electrical current generator; integrating and synchronizing, with the CCD processor and at least one algorithm, input data to generate a GVS profile, translating the GVS profile, with the CAD processor into a current application profile; generating with the CAD electrical current generator a stimulation current according to the determined current application profile; and providing the generated stimulation current to the subject with at least two of the electrodes to provide a perceived motion to the subject in at least one dimension or direction.

Yet another embodiment of the present invention includes a method of providing galvanic vestibular stimulation (GVS) to a subject to provide perceived motion, the method comprising steps of: providing to the subject a GVS system comprising a human interface device (HID), a central control device (CCD) and a current application device (CAD), the HID comprising a modified eyewear or eyeglasses apparatus with at least two dry forehead electrodes and at least two dry ear electrodes, each electrode comprising an upper surface and a lower surface with a plurality of surface features disposed on the lower surface, the CCD comprising a processor comprising at least one algorithm, and the CAD comprising a processor and an electrical current generator; integrating and synchronizing, with the CCD processor and at least one algorithm, input data to generate a GVS profile, translating the GVS profile, with the CAD processor into a current application profile; generating with the CAD electrical current generator a stimulation current according to the determined current application profile; and providing the generated stimulation current to the subject with at least two of the electrodes to provide a perceived motion to the subject in at least one dimension or direction.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in and constitute a part of this specification. The drawings illustrate various embodiments of the invention and together with the description serve to explain the principles and operation of the many embodiments of this invention.

DETAILED DESCRIPTION

Figure 1:
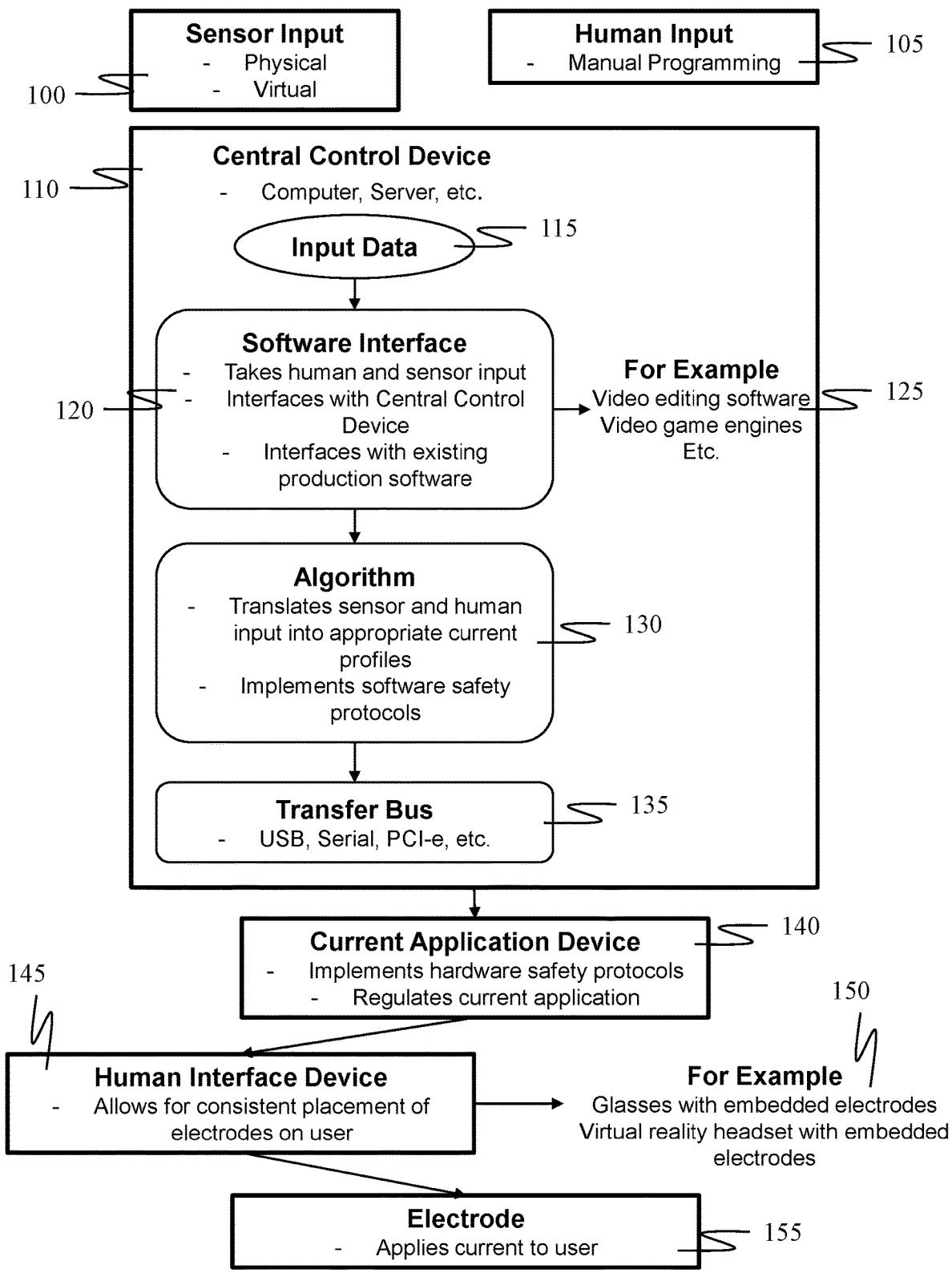
FIG. 1. Flow chart depicting operation of a preferred embodiment of a system and/or method for processing input to develop and provide GVS to a subject.

The present invention is directed to systems, devices and methods for stimulating perceived motion, and more particularly to stimulating perceived motion in three axes. The invention is further directed to stimulating such perceived motion when accompanied by visual stimuli. The invention is further directed to utilizing as few as two distinct pairs of electrodes to administer electrical stimulation to generate the perceived motion. The invention is further directed to systems, devices and methods to minimize side effects while utilizing electrical currents create the perceived motion. The systems, devices and methods of the present invention are further preferably useful or adaptable for other applications including transcranial direct current stimulation (tDCS).

Many embodiments of the present invention utilize electrodes to provide electrical stimulation to a subject. Electrodes of any type or variety may be used in conjunction with the present invention. Depending on the placement of a particular electrode, traditional "wet" electrodes may be used wherein a conductive paste, gel, fluid or semi-solid may be applied to the subject's skin and the electrode placed on the conductive gel, fluid or semi-solid in order for the gel, fluid or semi-solid to facilitate the transmission of the electrical current and reduce impedance. Alternatively, some electrodes come with such conductive gel, fluid or semi-solid pre-applied, thus reducing the number of steps required for a user to apply the electrode(s) to the subject's skin. Alternatively or in conjunction with the conductive gel, the subject(s)' skin may be mechanically abraded, the electrode may be amplified. Further additionally or in conjunction with the above skin preparation techniques, dry electrodes may be used. Physiological recording electrodes of the type described in U.S. Pat. Nos. 6,782,283, 6,785,569, 7,032,301, 7,286,864, 8,201,330, 8,428,682, 8,201,330, and 9,192,313, as well as in U.S. patent application Ser. No. 13/845,749, filed on Mar. 18, 2013 but at this time unpublished, are herein incorporated by reference. Dry electrodes provide the advantage that there is no gel to dry out, no skin to abrade or clean, and that the electrode can be applied in hairy areas such as the scalp. These electrodes may be particularly useful for embodiments where an electrode is placed on the back of the subject's head or neck, thus minimizing or eliminating the need to clear the area of hair before applying an electrode. Preferably the electrode(s), and particularly dry electrode(s), comprise surface features that are designed to facilitate conduction of electrical signals to and from the electrode. Such surface features further provide the benefit of reducing side effects such as cutaneous sensation in the subject, for example minimizing perturbations or aggravation on the subject's skin such as burning or tingling sensations, particularly when compared to traditional gel-based or other "wet" electrodes. Preferably the electrodes are designed and produced in a manner that enhances electrical current flow at the electrode skin interface such as increasing the paths of lower resistance so that the current is better distributed over a larger area or at more discrete sites designed into the electrode. The dry electrodes may be further designed to accommodate a gel, fluid or semi-solid coating to further reduce side effects.

Some embodiments that utilize a gel, fluid or semi-solid to coat the lower surface of the electrode that comes into contact with the subject's skin may do so to facilitate iontophoresis. Iontophoresis is the physical diffusion of charged molecules or particles (ions) through a medium driven by an applied electrical field. Iontophoretic embodiments preferably apply this process to deliver a numbing agent, such as an anesthetic or analgesic (e.g., lidocaine or the like), into the subject's skin in order to minimize discomfort from surface features of the electrode and/or side effects from the provided electrical stimulation, such as dermal effects. Iontophoresis allows the systems or devices to use the provided electrical stimulation current to drive the numbing agent through the gel, fluid or semi-solid and into the subject's skin, thus delivering and applying the agent to the subject's skin so it can take its desired effect. Alternatively, a separate electrical field may be used to first diffusively drive the numbing agent to the subject's skin, and then separately provide the stimulation current once the skin has been numbed. Generally, iontophoresis is performed by driving a charged substance, such as the anesthetic or analgesic, transdermally by repulsive electromotive force, through the skin. A small electric current is applied to an iontophoretic chamber placed on the skin, containing a charged active agent (the numbing agent) and a solvent. Another chamber or a skin electrode carries the return current. One or two chambers are filled with a solution containing an active ingredient and it's solvent. The positively charged chamber (anode) will repel a positively charged chemical species, whereas the negatively charged chamber (cathode) will repel a negatively charged species into the skin. This process allows the system to provide an anesthetic or analgesic for embodiments that do not use conductive coatings such as a gel, fluid or semi-solid (e.g., silver/silver-chloride) or separately from the gel, fluid or semi-solid, though in some embodiments the anesthetic or analgesic may be diffused into the electrolytic gel, fluid or semi-solid, and thus would not use iontophoresis.

The electrodes of the present invention are applied to a subject, which can be an animal or human body having skin comprising an epidermis comprising a stratum corneum layer and lower layers of the epidermis, and a dermis. The electrodes of the present invention further preferably comprise at least one surface feature on the lower surface of the device, the surface that comes into contact with the subject's or patient's skin. The surface feature(s) increases the surface contact with the skin and transforms a portion of the ionic current into an electric voltage that can be transmitted through these individual surface feature(s). The surface features further enhance the stability of the device when placed on the subject's or patient's skin, and serve to decrease electrical impedance, thus facilitating transmission of a stronger, higher quality signal.

The electrode of the present invention has an upper and a lower surface. The lower surface of the electrode is preferably the surface that comes into contact with the patient's or subject's skin, when the electrode is placed onto the patient or subject. The lower surface may take on many shapes or arrangements, and may further include a number of surface features for compressing, displacing, cracking, or perturbing the stratum corneum or outer layer of the epidermis, and accessing the lower layers of the epidermis, thus decreasing the electrical resistance and aiding in the establishment of the electrical pathway from the electrode through the skin. The skin comprises a layer of dead skin cells that is a source of very high impedance and limits conduction of electrical signals and currents through the skin. The surface features help to displace or compress this layer of cells in order to reduce the impedance and facilitate conduction of the electrical signals and currents through the skin. Some types of surface features may pierce this layer and provide a direct pathway to the more moist and conductive layers below. This moist layer will then provide fluid to the high impedance skin features which will aid in electric current flow once moist. Other types of surface features may compress this layer of cells to make it more compact, while also causing moisture from the layers of cells below to well or travel up into the non-conductive outer layer, thereby further increasing the conductivity through the increased presence of moisture. Various embodiments may utilize one or a combination of types of surface features on each electrode used. These surface features may take one of many forms including but not limited to ridges, columns, penetrators, anchors, epidermal stops and combinations thereof. These surface features, in general, protrude from the various shaped substrates described above. Preferably, there is at least one structure or surface feature protruding from the device's lower surface. More preferably, there are at least two structures or surface features protruding from the device's lower surface. Yet more preferably, there are at least three structures or surface features protruding from the device's lower surface. Still more preferably, there are at least four structures or surface features protruding from the device's lower surface. Even more preferably, there are at least five structures or surface features protruding from the device's lower surface. Still yet more preferably, there are at least six structures or surface features protruding from the device's lower surface. Yet even more preferably, there are at least seven structures or surface features protruding from the device's lower surface. Even still more preferably, there are at least eight structures or surface features protruding from the device's lower surface. Yet still more preferably, there are at least nine structures or surface features protruding from the device's lower surface. Still even more preferably, there are at least ten structures or surface features protruding from the device's lower surface. Even yet more preferably, there are at least eleven structures or surface features protruding from the device's lower surface. Most preferably, there are at least twelve structures or surface features protruding from the device's lower surface. The presence of more surface features, especially non-penetrating surface features, creates more compression of the high-impedance layer of skin, and thus decreases the impedance over a greater area and leads to greater conductivity for electrical signals and currents. One of the important secondary functions of the configuration of surface features is to displace or move the hair, dead skin cells and/or detritus so that the surface features can better send electrical stimulation into the skin. Another secondary function of the surface features and their configuration is to increase the surface area of the electrode portion that is in contact with the subject's skin. Greater electrode conductive surface area of contact with the skin serves to further facilitate the conduction of electrical signals and currents through the skin and may help reduce the occurrence of side effects such as dermal effects.

The electrode of the present invention comprises an upper and a lower surface. The lower surface can take many forms. For instance, the lower surface can be flat, concave, convex, or some other unique shape. The electrode can be substantially flat on its lower surface. Various embodiments of the present invention could include changes in the electrode's lower surface. Whether the lower surface is perpendicular to the device's vertical axis or sloped depends on the application. The electrode can also be substantially concave on its lower surface. An example is where the lower surface is inwardly curved like a portion of the inner surface of a large sphere. The electrode can also have a convex shape on its lower surface. An example is where the lower surface curves or bulges outward, like a portion of the exterior surface of a large sphere. The lower surface of the electrode is not limited to one of the aforementioned shapes, and may take on a number of other unique shapes or some combination of the shapes listed above.

The lower surface of electrode of the present invention may further include a number of surface features for displacing, cracking, or perturbing the stratum corneum or outer layer of the epidermis and accessing the lower layers of the epidermis. Such displacing, cracking, or perturbing of the skin may include the surface features physically penetrating the stratum corneum and accessing and physically contacting the lower layers of the skin. However, it may be preferable for the surface features to merely perturb, stretch, or open the stratum corneum by cracking or displacing it without actually physically penetrating it, in order to provide a lower electrical resistance pathway from the lower layers of the skin to the electrode. The penetrating surface features can take many shapes including but not limited to pyramidal, needle-like, triangular, or any other shape that can be tapered to a point or tip. Preferably, the size and shape of the penetrator is such that the penetrator(s) will not break or bend during normal use, will limit the depth the penetrator enters the skin under typical application conditions, and/or will anchor the device to prevent motion artifacts or any substantial movement. Such surface features are explained in detail in U.S. Pat. No. 6,785,569 to Schmidt et al, which is herein incorporated by reference. These surface features may take one of many forms including but not limited to ridges, columns, penetrators, anchors, epidermal stops and combinations thereof. These surface features, in general, protrude from the various shaped substrates described above. Preferably, there is at least one structure or surface feature protruding from the device's lower surface. One of the important functions of the configuration of surface features is to displace or move the hair, dead skin cells and/or detritus so that the surface features can better send the electrical signals through the skin. Another function of the configuration of the surface features is to minimize discomfort or to enhance comfort.

The ridge(s) as used in the present invention is preferably a long, narrow structure or elevation. The ridge(s) can have a variety of cross sections over a length. Examples of these cross sections include but are not limited to a square, rectangle or trapezoid, a pointed surface like that of a triangle, a domed surface like that of an arch or arc, a cross section with a concave surface between to ridge lines forming the two ridge lines, some other unique cross-section or the like. The cross section of the ridge extends for a length. The length of the ridge is preferably substantially longer than the height or width of the cross-section of the ridge. The surface of the ridge away from the substrate, when applied to the skin surface, depresses, but does not need to penetrate the skin but anchors the device in place to prevent motion artifacts, to displace hair, dead skin cells and/or detritus, to increase the surface area of the device in contact with the skin, and to be capable, in part, of transmitting an electric potential which can be measured from the surface of the skin through the ridge.

A column(s) is another type of structure or elevation that can be used in the present invention. A column(s) can have a variety of cross sections over a length. Examples of these cross sections include but are not limited to a square, rectangle or trapezoid, a pointed surface like that of a triangle, a domed surface like that of an arch or arc, a cross section with a concave surface between two points (wherein the distance from the base to either point is greatest height of the column for the cross-section), some other unique cross-section or the like. The cross section of the column like a ridge extends for a length. However, the width of the column is preferably in proportion to the height of the cross-section of the column, and more preferably shorter than the height of the column. The surface of the column away from the substrate, when applied to the skin surface, depresses, and does not easily penetrate the skin but anchors the device in place to prevent motion artifacts, to displace hair, dead skin cells and/or detritus, to increase the surface area of the device in contact with the skin, and to be capable, in part, of transmitting an electric potential which can be measured from the skin through the ridge.

A penetrator(s) is also a surface feature that can be used in the present invention. The penetrator(s) is sized and shaped for displacing, cracking, or perturbing the stratum corneum or outer layer of the epidermis, and accessing the lower layers of the epidermis. The penetrator can take many shapes including but not limited to pyramidal, needle-like, triangular, or any other shape that can be tapered to a point or tip. The surface of the penetrator away from the substrate, when applied to the skin surface, readily penetrates the skin, preferably anchors the device in place to prevent motion artifacts or any substantial movement, increases the surface area of the device in contact with the skin and lower layers of the epidermis, and is capable, in part, of transmitting an electric potential which can be measured from the skin and lower layers of the epidermis through the penetrator.

The epidermal stop(s), which can be used in the present invention, is a structure or elevation. Epidermal stops are structures of a particular height with respect to the height of the penetrator(s) or other surface features so as to prevent the penetrator(s) or other surface features such as columns and ridges from penetrating into the dermis of the skin or unduly distorting the surface of the skin, respectively, where they might cause discomfort to the subject. An epidermal stop(s) may also be incorporated into a penetrator, ridge, and column or like surface feature or can be a separate surface feature. The epidermal stops may, however, have any shape known to those skilled in the art that would effectively prevent the penetrator(s) from entering the dermis of the skin, or from being applied to deeply. The epidermal stops are preferably applied in an array among the penetrators, therefore further minimizing inadvertent deep penetration or over penetration by the penetrator(s) or minimizing significant distortion of the skin by other surface structures. If the epidermal stop is a separate surface feature or incorporated into another structure, preferably, the epidermal stop in combination with at least one other surface feature or two structures with incorporated epidermal stops create a detritus trough.

A detritus trough is the area interposed between adjacent surface structures or features. These troughs, when provided or naturally occurring in the design, allow for a more accurate placement of the surface features by allowing for displacement of the hair and other detritus on the skin in these troughs. Preferably, the detritus troughs are sufficient in number and size to allow for placement of the device on skin with a significant amount of hair such as for example the scalp or the chest of a male subject. Detritus troughs are created to maximize the area available for optimal device to skin contact, by improving the probability that hair and other detritus will enter the troughs and not preventing the surface features from either coming in contact with the skin or penetrating the skin. Thus detritus troughs may be parallel to one another, perpendicular to one another, or in any other orientation made to improve the contact of the device with the skin of the subject. This detritus trough may also function as a means to store fluids or other substance to minimize side effects associated with electrical stimulation or discomfort.

An anchor(s), which can be used in the present invention, is a structure or elevation that stabilizes the physiological device against a subject's skin. This stabilization further preferably prevents motion artifacts in the electrophysiological signal from the device, or any substantial movement. While the anchor can also be any of the structures described above, the anchor may also serve no other purpose except to stabilize or reduce movement of the device on the subject's skin. The anchor(s) can have a variety of cross sections over a length as described above for the various surface structures.

The ridges, columns and penetrators also increase the amount of surface area of the skin in contact with the electrode, which is applied. This allows for greater pick up of (or stronger) signals from the skin's surface, and further allows for the electrode to be better anchored to the subject's skin resulting in less artifacts to the signal through movement and the like. The electric voltage from these surface features is measured using conventional measuring devices.

The electrode further comprises an upper surface which is the surface that faces away from the patient or subject when the electrode is applied to the patient or subject. Preferably, the upper surface comprises some variety of connector used to connect the electrode to stimulation equipment, and to complete an electrical pathway through the patient to said monitoring equipment. The connector may be of any variety commonly known to those of skill in the art currently, or later developed. Examples of such connectors include, but are not limited to, snap connectors, button connectors, tension or compression fittings, and the like. Further, the upper surface of the electrode may take on many shapes and configurations, for example it may be a flat surface, or may be curved in a convex or concave manner.

Electrode configuration is an important consideration when designing the various embodiments of the present invention. When injecting an electrical current into a subject through an electrode, the electrical current may have a tendency to concentrate around the circumference or perimeter of the electrode conductive region. This can lead to increased side effects as well as difficulties in directing the electrical current along the desired electrical pathway. The inclusion surface features contacting the subject's skin is one way to address this effect by increasing the number of contact points between the electrode and the skin and creating a number of circumferences or perimeters that are much smaller and disposed across the surface of the electrode. The shape or perimeter of the electrode may be modified to include configurations that aid the distribution of the electrical current over the electrode surface and into the skin. Examples of various perimeter shapes include but are not limited to circles, squircles (squares with rounded corners), ovals, pedestals, gears or other shapes that enhance current flow into the skin. Additionally, multiple electrodes may be placed at a given electrode placement site. This further increases the surface area, contact points beneath the surface features and circumference or perimeter of the electrode at a particular stimulation site which, as noted, will increase conductivity through the skin, particularly when the multiple electrodes each have a number of surface features, and reduces side effects. Multiple electrodes, each with a number of surface features, may increase the overall conductive surface area at the electrode side exponentially allowing for a greater reduction in skin impedance, and a greater increase in control of the electrical current being supplied. Further, more than one electrode may be electrically connected, and optionally mechanically connected such as by inclusion on a common substrate (e.g., patch), and thus characterized as a single electrode in relation to the operation of the system and its various stimulation profiles or protocols.

Additional embodiments of electrode configuration include utilizing various coating patterns on the surface of the electrodes to distribute the electrical current over the entire surface of the electrode instead of at the circumference or perimeter of the electrode conductive region. The manner in which the electrode is coated will enhance current distribution along with the edges of the conductive material on the surface of the electrodes in a manner to enhance current flow through the skin. The coating may appear as circular rings on the surface that are all electrically connected. By creating these concentric circular conductive rings, the current will flow to the edges of each ring which will improve current distribution over the electrode surface. Multiple concentric rings are envisioned. This embodiment includes other patterns made by conductive coatings or materials on the surface of the electrodes. Examples of other pattern embodiments include, but are not limited to, spirals, serpentine shapes and the like. Examples of conductive coatings or materials to create the patterns include Ag/AgCl, gold, silver, nickel, copper or other such conductive material. In this embodiment, the current will flow into the skin along the edges of the conductive material and the contact points beneath the surface features. These coatings may be applied using additive and subtractive techniques commonly used to apply inks onto substrates or electronic components such as pad printing, vapor deposition, painting or other coating process where a mask or a sacrificial material may be used to create the desired patterns. These conductive coatings and materials may be placed on top of the surface features further improving current flow into the skin and distributing current over the electrodes. Coatings of electrically conductive compounds are not necessarily required on all embodiments of the electrodes. Some electrodes may be constructed of metal, and thus be electrically conductive inherently. Alternatively, some embodiments with metal electrodes may include a conductive coating.

Another embodiment of the invention is to include conductive pathways through the thickness of the electrode. These through thickness conductive pathways are envisioned to be located throughout the surface of the electrode and more preferably located within a surface feature and more preferably located in the center of a surface feature. These through-thickness conductive pathways or columns are electrically isolated from adjacent columns and hence is only electrically conductive in the thickness direction. This embodiment will further improve the distribution of current over the electrode surface in contact with the skin. The single or multiple conductive through thickness columns will be connected on the side opposite the skin to uniformly send current to each of the through thickness columns. To further improve current flow, these conductive columns will be integrated within the surface features. This embodiment will distribute the current to each surface feature which will compress the skin at the contact point further improving current flow into the skin.

A further embodiment is the manner in which the through thickness electrically conductive columns are produced. These columns may be co-molded into the substrate material. Other manufacturing embodiments include utilizing a roll-to-roll process. The roll-to-roll process will create the conductive through thickness columns, will create the desired surface features and will further improve the distribution of current over the electrode surface. The through thickness conductive columns are produced by placing the film within a magnetic field. The magnetic field aligns the conductive particles in columns in the thickness direction of the film. In various embodiments, the conductive particles may be nickel nanoparticles and nanoflakes. In other embodiments, the conductive particles may be steel balls coated with gold silver or other conductive material which will be aligned in the magnetic field. Further, the magnetic field could be utilized to naturally raise the conductive particles above the substrate surface creating protrusions out of the film plane under the action of magnetic field, producing the desired surface features that are required for appropriate signal transmission through the skin. This process will enable the surface features and conductive, through thickness, columns to be optimized during the roll-to-roll process. These aligned columns allow for large number of conductive pathways to occupy very small space hence parallel current pathways are facilitated. Because these electrodes can be produced with any polymer matrix (rigid, flexible, elastomeric), performance can be tuned to the desired application. Flexible electrodes via this process will be connected to a means to send the current into the skin with printed interconnects, further reducing cost and complexity. Further, the roll-to-roll process may include coatings and interconnects within the manufacturing line which will further reduce the cost while enabling the electrodes to be manufactured reliably in large volumes. This embodiment offers a unique opportunity to create a large number of conductive pathways distributed through the electrode at a very low cost, while also enabling robust sensor design by interconnecting any of these arrays of columns. This flexible platform technology will enable low-cost, comfortable electrodes to be readily integrated into the Human Interface Device (HID). These electrodes may be snapped in and out of the HID making the electrodes disposable in order to minimize contamination between users.

Another embodiment is to utilize a flexible/stretchable substrate as the electrode. These flexible substrates will be injection molded, will be included in a roll-to-roll process or other polymer fabrication process including but not limited to machining, stamping etc. The use of flexible or bendable substrates will enable the electrode to better conform to the skin topography to increase the contact with the skin. Further, the flexible substrate will increase the surface area and/or distribute the pressure over the area of the electrode. These flexible substrates can be made from any type of material that enables the electrode to bend or flex such as but not limited to rubbers, elastomers, semi-rigid polymers. Further these flexible substrates can include through thickness conductive columns or be coated with a conductive material to improve current flow. Other embodiments may include adding fillers or conductive matter into the substrate or utilizing conductive polymers.

The electrodes may be placed against the subject's skin in numerous ways. One option is to affix the electrodes themselves directly to the subject's skin. Such attachment may be achieved utilizing an adhesive, preferably temporary, on the lower surface of the electrode that adheres or binds the lower surface of the electrode directly to the subject's skin, or on an adhesive collar that surrounds the lower surface of the electrode and adheres to the subject's skin holding the electrode in place. In such embodiments, the adhesive may be used alone to coat the lower surface, including all or a portion of any surface features present, or may be combined with other fluids, gels or semi-solids such as a conductive coating (e.g., silver/silver-chloride or the like), medications (e.g., anesthetics or analgesics), or other such substances. Alternatively, the electrodes may comprise a mechanism whereby the electrode is caused to be pressed or held against the subject's skin, such as by pressure placed against the electrode perpendicular to the subject's skin, or by suction, such as by a hood or cover around the electrode that suctions to the subject's skin and pulls the electrode and skin together, holding the electrode in place.

Another alternative is to place the electrodes in contact with the subject by attaching them to a wearable system or device that the subject may don and wear and which holds the electrodes against his or her skin. This human interface device (HID) or wearable system or device may take many forms in various embodiments. One embodiment of a wearable electrode system or device is a patch that can be placed on the subject's skin and which has at least one electrode attached to, affixed to, or embedded in the patch. Preferably, the wearable electrode system or device, and particularly in patch embodiments, comprises a flexible substrate to which the electrode(s) are attached, affixed or embedded into. The flexible substrate, which may be composed of an elastomer or rubber, when placed on the subject's skin, adjusts and flexes in order to match the contours of the subject's skin at the placement location. This adjustment and flexing allows the wearable system or device to keep the electrode(s) of the wearable system or device placed against the subject's skin securely, maximizing the surface area of contact between the electrode and the skin, and preferably maintains this secure, stable contact during movement by preventing the electrode(s) from lifting or separating from or shifting on the subject's skin. Patch embodiments of the wearable electrode system or device may be attached to the subject with an adhesive that surrounds the electrode(s) and an area around the electrode(s) holding the electrode(s) to the subject's skin. Alternatively, a harness or garment wearable electrode system or device may be used in some embodiments. Harnesses, such as those described in U.S. Pat. Nos. 8,019,402, 8,954,129, 9,326,695, and 9,572,506, which are hereby incorporated by reference, may be used or adapted to be used in accordance with the present invention.

The human interface device (HID) preferably have at least one electrode attached to, affixed to or embedded into the harness or garment, and are adapted to be worn by the subject thus placing the electrode(s) in contact with the subject's skin and holding it in contact while the harness or garment is worn. Similar to the patch described above, preferably harness or garment embodiments comprise a flexible substrate adapted to flex and adjust to match the contours of the subject's skin, and to maintain contact between the electrode(s) and the skin while being worn even if the subject moves or shifts. Some embodiments of harness or garment systems or devices may include a rigid backbone component embedded into the garment at electrode placement sites that are adapted to place additional pressure to the back of the electrode, perpendicular to the contact plane between the electrode(s) and skin, and to hold the electrode(s) in contact with the skin. Further, some harness or garment embodiments may comprise a track system, such as described in U.S. Pat. No. 9,326,695 to allow the electrodes to be adjusted or moved within the garment or harness. Such adjustment allows for precise placement of the electrode(s) in a desired location on the subject's body as well as allows the electrode(s) to remain in place during movement or flexing such that if the subject moves and the harness or garment shifts, the electrode may remain in place against the skin while the harness or garment shifts and the electrode shifts slightly along the track system of the harness or garment. Harness or garment embodiments may utilize adhesive, but more preferably are designed to be worn and surround the subject in a manner that provides pressure holding the electrode(s) in place and in contact with the skin. The harness or garment, with or without the track is envisioned to enhance comfort, adjust electrode location to enhance the perceived motion, to minimize side effects and/or to accommodate multiple sizes of subjects. Examples of harness or garment embodiments include, but are not limited to, harnesses, headgear (e.g., caps, hats, headbands, hat/helmet liners, ear muffs, ear protection, and the like), or other such systems or devices. Still a further alternative is for the electrode(s) to be attached to, affixed to, or embedded in a wearable accessory system or device. Examples of such accessory systems or devices include, but are not limited to, eyewear, 3-D glasses, armbands, hearing aids, earmolds, ear clips/ear rings, head bands, hair bands, hairclips, and the like. Wearable electrode accessory systems or devices such as those described in U.S. patent application Ser. Nos. 14/571,733 and 14/571,856, each filed on Feb. 18, 2014 but not yet published, and U.S. Pat. No. 9,579,060, which are herein incorporated by reference, may be used in accordance with the present invention. Each particular embodiment of such systems or devices calls for varying methods of placing the electrode(s) in contact with the subject's skin and maintaining such contact during use; however, adhesives, pressure and or suction may be used alone or in combination for each system or device and each electrode. The accessories may have electrodes attached to or embedded into the accessory such that when the accessory is donned, the electrodes are put in contact with the subject's skin and such contact is maintained while the system or device is worn by the subject.

When placing electrode(s) in contact with the subject's skin, one particularly problematic issue is the presence of hair on the subject's skin. This is particularly problematic for electrode(s) placed on the subject's skin, but different subjects have different amounts, thicknesses, densities, and styles of hair located on various parts of their body where electrodes may be placed. One option is to shave the hair from the desired electrode placement location; however, this clearly is not a preferred solution for repeated uses—for example, it does not make sense for a subject to enter a movie theater and shave an area of his or her head in order to place an electrode for a perceived motion system to enhance the movie-viewing experience. Thus, the methods and systems of the present invention preferably are able to move or displace hair, temporarily, and without removing hair, yet still place an electrode that achieves and maintains good contact with the subject's skin. The surface features as described herein are one feature that helps with this issue. The various surface features may part the subject's hair and come into contact with the skin beneath the hair while the hair is moved out of the way of the lower surface of the electrode or travels between the surface features allowing the surface features to still contact the skin. Some embodiments may utilize an electrode applicator that is adapted to move hair out of the way as it applies an electrode to the skin. One embodiment of an electrode applicator may be an "electrode stamp" that houses one or more electrodes until ready to apply to skin, and then is applied to the skin at the desired location and operated to, in as little as one motion, brush or move hair out of the way, apply a fluid, gel or semi-solid to the surface of the electrode, and apply the electrode to the subject's skin. The electrode stamp preferably comprises a brush or comb component which is adapted to part or move hair on the subject's body at the electrode application location. The electrode stamp also preferably comprises a well, reservoir or application mechanism which applies the fluid, gel or semi-solid to the surface of the electrode to achieve better current flow. The fluid, gel or semi-solid may be a single compound or a mixture of such including, but not limited to, conductive compounds or coatings (e.g., silver/silver-chloride [Ag/AgCl], gold, or the like), anesthetics or analgesics to increase the comfort at the electrode sight and minimize side effects such as dermal effects and discomfort from the surface features (e.g., lidocaine or the like), and the like. As the electrode stamp is placed against the skin and operated, such as by applying pressure to the stamp, much like an ink stamp, the electrode stamp operates to move the electrode into place while applying the fluid, gel or semi-solid, and to move or part the hair such that as the operation of the electrode stamp is completed, a prepared electrode is put into place on the skin with minimal hair between the electrode and the skin. For embodiments where the electrodes include surface feature(s), the fluid, gel or semi-solid is an optional element because the surface features, as noted herein, operate to reduce impedance and increase conductivity (such as by compressing the high-impedance layers of the skin, releasing moisture, and creating numerous electrical pathways with lower impedance), and thus may not require the addition of an electrolytic compound to increase conductivity of the electrical signal or current.

The systems and devices of many embodiments of the present invention include numerous components, including, but not limited to a central control device (CCD), a current application device (CAD), and a human interface device (HID). These devices could be either tethered with a physical wire, or wireless depending on the embodiment. The central control device, which is preferably a computer or processing device, for example a desktop computer for a video game application or a central server for a movie theater application, preferably takes in data from sensors (virtual or physical) or be manually programmed, translates this input to GVS stimulation profiles using software algorithms, and synchs these GVS signals with the accompanying visual media. The CCD preferably then transmits this information via the Transfer Bus (USB, Serial, PCI-e or otherwise) to the CAD. Once received by the CAD, the GVS signals are preferably then applied to the appropriate electrodes on the human interface device.

An electrical current generator is used to supply an electrical current through the electrode(s) and into the subject. The current generator preferably is designed to provide an electrical current at known parameters (e.g., amplitude, frequency, waveform, and the like), and which can be altered to change the nature of the current being provided. The current may be decided by a user and programmed into the current generator to be provided. More preferably, an algorithm or series of algorithms on a processor may be used to receive input data (e.g., corresponding to the visual media, measured from the subject, etc.) and to adapt the electrical current in real-time to provide a particular type and strength of perceived motion in any one or multiple dimensions or directions. Preferably, current application profiles are generated using a combination of software algorithms, and hardware implementation. The amplitude of current application at any given time preferably will not exceed a ±2.5 mA range. GVS current profiles can be generated either from manually programmed profiles, or from sensor data. Sensor input may include data measured from the user using sensors including, but not limited to, accelerometers, gyroscopes, physiological sensors such as electrooculographic (EOG) sensors, electrocardiographic (ECG, EKG) sensors, electroenecephalographic (EEG) sensors, electromyographic (EMG) sensors, and the like. Virtual sensor data may also be used as an input to the current generation algorithm(s). Virtual sensors may include inputs from external systems (in relation to the subject) such as measured forces or movements of a player avatar in a video game. The system also preferably allows for manual programming via a software interface that allows users or other content creators, such as video editors, programmers, and the like, to easily add GVS functionality to their content. Sensor data is then run through a series of algorithms and filters to ensure that only desired perceived motion is achieved, while maintaining user safety and comfort. At a very high level, the filters and algorithms will take in data, remove noise and unwanted signals, and perform a series of heuristic operations to determine the base stimulation profile to achieve the desired proprioceptive effect (i.e., perceived motion). The algorithm(s) will also endeavor to accurately synchronize visual stimuli and the generated GVS profile. The program will create a current profile that will then be encoded by a central control device (CCD) and sent to a current application device (CAD) over a transfer bus. Once the CAD receives the GVS profile with accompanying synchronization parameters, the CAD will begin implementing the profile. While it is doing so, the CAD will continuously monitor output currents to ensure that the profile is being accurately represented, and will simultaneously perform safety checks to ensure that over-application of current is avoided. The CAD will perform these operations in a highly-deterministic fashion, as to maintain low latency and synchronization.

The central control device (CCD) may be responsible for integrating sensor data and manual input data, and may take the form of any computing or processing device such as a desktop computer, server, laptop computer, tablet computer, cell or smartphone, or the like. The CCD polls data from input devices at a pre-determined rate in order to maintain deterministic timing control of the system, and accordingly, the synchronization of GVS application with the accompanying visual stimuli. The CCD preferably comprises a software interface that processes programmed and sensor input using specially optimized algorithms and heuristics. These algorithms are responsible for producing appropriate GVS profiles for the given input data, as well as ensuring user safety through software interlocks. The software architecture may interface with existing software paradigms, such as video editing software and video game engines to ensure easy programming and implementation on the content creation side, and may run this content on the consumer side. GVS profiles would be created in software to allow for easy changes to algorithms and continued support over the product lifecycle.

The current application device (CAD) may be responsible for translating data generated by the CCD from input data into applicable current application profiles for providing current to the subject. The device is a highly integrated embedded system, with high determinism to ensure appropriate visual/stimulation synchronization. The CAD is also responsible for applying appropriate current values to the subject via a human interface device (HID) and accompanying electrodes. As such, there are preferably many hardware feedback and control loops present to prevent accidental over-administration of current to the user. The system preferably communicates regularly with the CCD over the Transfer Bus in order to maintain high determinism and synchronization.

The processing architecture of the CAD is preferably an ARM based microprocessor, which preferably communicates with the CAD over the Transfer Bus. The microprocessor preferably interfaces with one or more current-driving Operational Amplifier (Op-Amp) circuits via one or many Digital to Analog Converters (DACs). The Op-Amp circuits preferably then drive the appropriate amount of current, ranging from −2.5 to 2.5 mA, to the electrodes on the HID. Feedback and control loops preferably present in the hardware implementation preferably ensure that correct amount of current is being applied, and the system will adapt as needed in order to correct for errors, minimize side effects and enhance perceived motion. The system preferably also has over-current protection, short-circuit protection, and input protection to ensure that no damage is done to the system, or to the user.

Power is preferably provided by a 60601-BF medical-grade isolated power supply, with overcurrent protection provided by LEM current sensors as well fast-acting emergency fusing. Electrical isolation between the Transfer Bus and the CAD is preferably achieved using medical-grade opto-isolators.

The Transfer Bus preferably is designed to be a data transmission system, device or component. The GVS profiles generated by the software running on the CCD would be transferred to the CAD via a transfer bus. This bus could take the form of a USB, Serial bus, PCI-e interface, or other appropriate technology. Various embodiments may utilize different transfer bus types depending on the timing required for a particular application and the capabilities of each type of transfer bus.

The human interface device (HID) is preferably responsible for positioning electrodes in the required location on the users head. The device should also be easily placed on, and removed from, the subject's head. For some embodiments, such as a public movie theatre application or in-home television viewing or video game applications, the HID may take the form of modified glasses or eyewear. Alternatively, a custom headset may be developed to incorporate all the necessary elements of the present invention and to maximize the subject's comfort, ease of use, and enjoyment. Yet another alternative is for the HID to be integrated into existing Virtual Reality (VR) headgear, such as the Oculus Rift. Other examples of HID embodiments include the electrode placement systems and devices described above, including harness or garment embodiments and accessory embodiments.

The HID may preferably include the electrodes and/or sensors, or the electrodes and/or sensors may be separate and attached to the HID when ready for use. In a preferred embodiment, four electrodes may be included, with, for example, two electrodes adapted to be clipped to each of a subject's ears and two to be put in contact with the subject's forehead. The HID may interface with the CAD through wired communication such as a four conductor cable, which preferably is disconnectable, or through wireless communication.

Some embodiments of the HID may be designed to include a "self-adjustment" capability that would allow a subject or user to tune the system as part of an initial setup step or prior to any individual use of the system. Self-adjustment or tuning allows the user to alter the stimulation protocols in order to fit a particular need or desire, or set of needs or desires, for a given instance of use of the system. The subject or user may be able to select from a set of predefined stimulation protocols applicable for different uses, or may be able to individually adjust various setting related to the stimulation protocol. For example, in a home-based entertainment system, the GVS system may be interfaced with or integrated into a piece of furniture (e.g., gaming chair) that has a user interface through which the user or subject can adjust the stimulation parameters. In such exemplary embodiment, the subject may be able to choose a protocol predefined for video games versus a predefined protocol for watching movies or television, or alter the settings manually. The predefined protocols may be determined during an initial setup for the particular user, or may be preset upon manufacturing. The self-adjustment or tuning methods allow for increased performance in the form of the subject's awareness of perceived motion, minimization of side effects such as dermal effects (e.g., by selecting a current that does not cause perceived sensations on the skin), flashing lights (e.g., by routing the stimulation around or away from the optic nerve), minimize or eliminate perceived tastes caused by certain stimulation protocols, and to overall increase the safety and performance of the system, such as by optimizing the current flow in light of user-specific and system considerations and constraints.

Other embodiments of the HID will contain a tri-axial accelerometer, EOG sensors and integrated software and data acquisition (DAQ) modules. These sub-systems will be able to record direction and amount of sway exhibited by the test subject with or without vestibular stimulation. The DAQ module will be sensitive enough to detect and measure balance and postural parameters of the test subject. This embodiment is of particular interest to detect mTBI because the amount of sway could otherwise go unnoticed by a medic performing a visual assessment of the patient's motor and balance skills. For this medical application, the latent postural recovery data collected by this HID will be evaluated to determine if the results are within an established threshold based on the subject's pre-baseline recovery times.

Now referring to the drawings, FIG. 1 is a flow chart depicting operation of a preferred embodiment of a system and/or method for processing input to develop and provide GVS to a subject. The system accepts multiple forms of input, including sensor input 100 and human or manual input 105. Sensor input 100 may include any type of data from sensors attached to or otherwise monitoring or measuring the subject in some way. Sensor input 100 may include physical sensors such as those that measure physiological signals from the subject (e.g., EMG, ECG/EKG, EOG, EEG, and the like), movement (e.g., accelerometers, gyroscopes, video sensors, and the like), or virtual sensors such as those that monitor or measure the movement of a virtual presence or entity such as a video game avatar. Human or manual input 105 includes such data that is manually entered into the system by a user or programmer and may include data such as demographic information of a subject, specific commands or desired variables or outputs, or programming related to the visual stimuli provided by the system. All input data 115, including both sensor input 100 and human or manual input 105, is entered into the central control device 110 (CCD) for processing. The CCD 110 may be any computing or processing device including computers, servers, tablets, cell or smartphones, and the like. The input data 115, again comprising at least sensor input 100 and/or human or manual input 105, is entered into the software interface 120 of the CCD 110. The software interface 120 combines the input data 115 and performs a first level of processing by interfacing the input data 115 with existing production software 125, such as video editing software, video game engines, and the like, and the CCD 110. The software interface then directs the input data 115 along with any alternative or additional information resulting from the interface to an algorithm or series of algorithms 130 for processing. The algorithm or series of algorithms translate sensor input 100 and human or manual input 105 into current stimulation profiles that are aimed at eliciting the desired perceived motion (proprioceptive effect) based on the input data 115. The algorithm(s) 130 further take into account safety protocols, for example current limits and pathways set to ensure the subject's safety, when computing the desired stimulation current profile or protocol. The current profiles or protocols are then output from the algorithm(s) 130 and transferred via the transfer bus 135 to the current application device 140 (CAD). The transfer bus 135 may be separate from or in wired or wireless communication with the CAD. The CAD 140, when providing stimulation according to the current profiles or protocols implements a second level of safety protocols to ensure the safety of the subject by, for example, limiting the amplitude, waveform and pathway of the provided current. The CAD 140 generates the desired electrical current according to the computed current profile(s) or protocol(s) and transmits the desired electrical current to the human interface device 145 (HID). The HID 145 can be of any type of device designed to apply electrodes 155 to the subject, and preferably to ensure consistent, repeatable, comfortable placement of the electrodes 155. Examples of HID embodiments 150 include glasses or eyewear with embedded or attached electrodes, a cap or headpiece with embedded or attached electrodes, and a virtual reality headset with embedded or attached electrodes, to name but a few. The HID 145 passes the desired electrical current to the electrodes 155 which in turn transmit the current to the subject.

Figure 2:
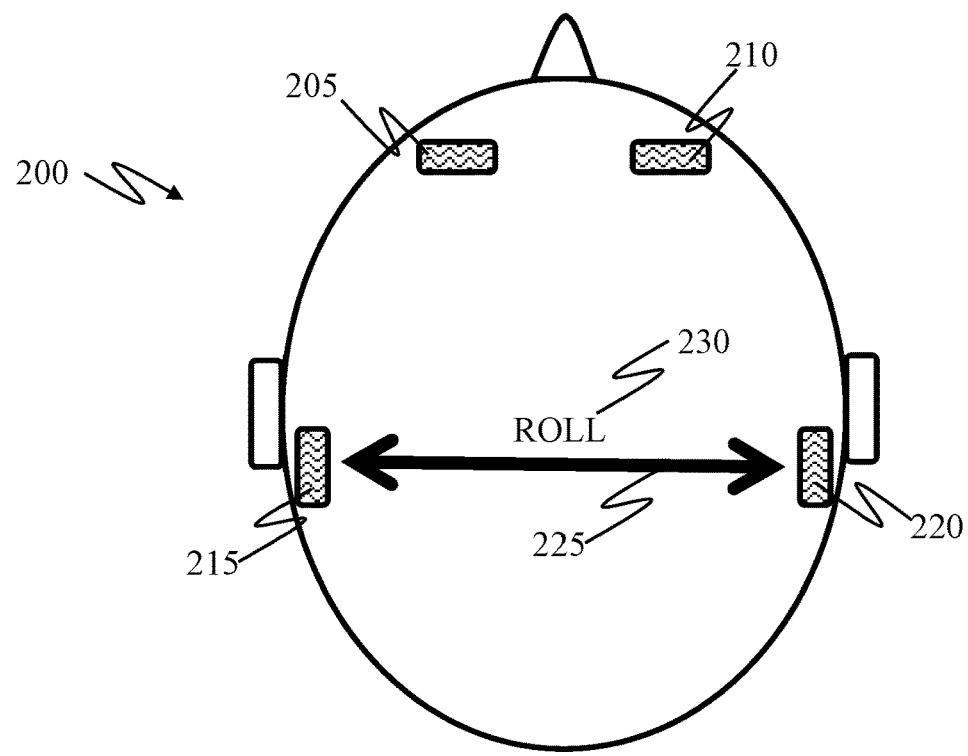
FIG. 2. Diagram depicting optional electrode placement and optional stimulation pathway to elicit perceived pitch motion.

FIG. 2 is a diagram depicting optional electrode placement and optional stimulation pathway to elicit perceived roll and yaw motions. The subject 200 has several electrodes applied to his or her head, preferably attached to or integrated into an HID (not shown). The depicted embodiment includes four electrodes, a left forehead electrode 205, a right forehead electrode 210, a left ear electrode 215 and a right ear electrode 220. The desired electrical stimulation current 225 is computed and applied between the left ear electrode 215 and the right ear electrode 220, and elicits a perceived roll 230 motion and a perceived yaw 235 motion for the subject.

Figure 3:
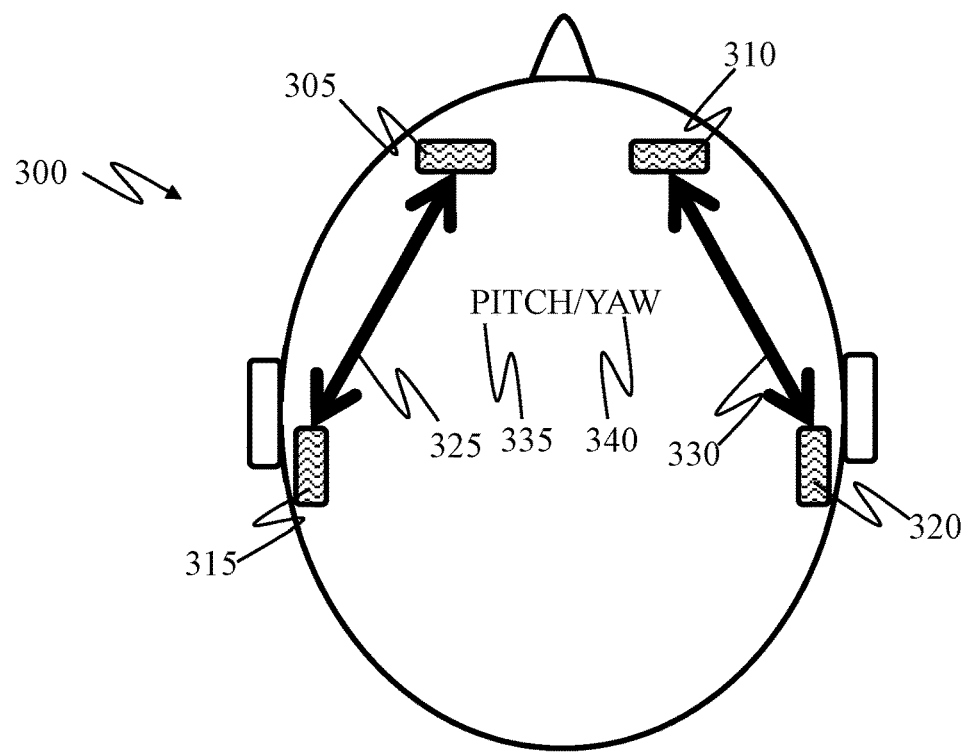
FIG. 3. Diagram depicting optional electrode placement and optional stimulation pathways to elicit perceived roll and yaw motions.

FIG. 3. Is a diagram depicting optional electrode placement and optional stimulation pathways to elicit perceived pitch motion. The subject 300 has several electrodes applied to his or her head, preferably attached to or integrated into an HID (not shown). The depicted embodiment includes four electrodes, a left forehead electrode 305, a right forehead electrode 310, a left ear electrode 315 and a right ear electrode 320. The depicted embodiment transmits electrical stimulation currents, a left current 325 applied between the left ear electrode 315 and the left forehead electrode 305, and a right current 330 applied between the right ear electrode 320 and the right forehead electrode 310, and this pair of currents elicits perceived pitch 335 motion for the subject.

Figure 4:
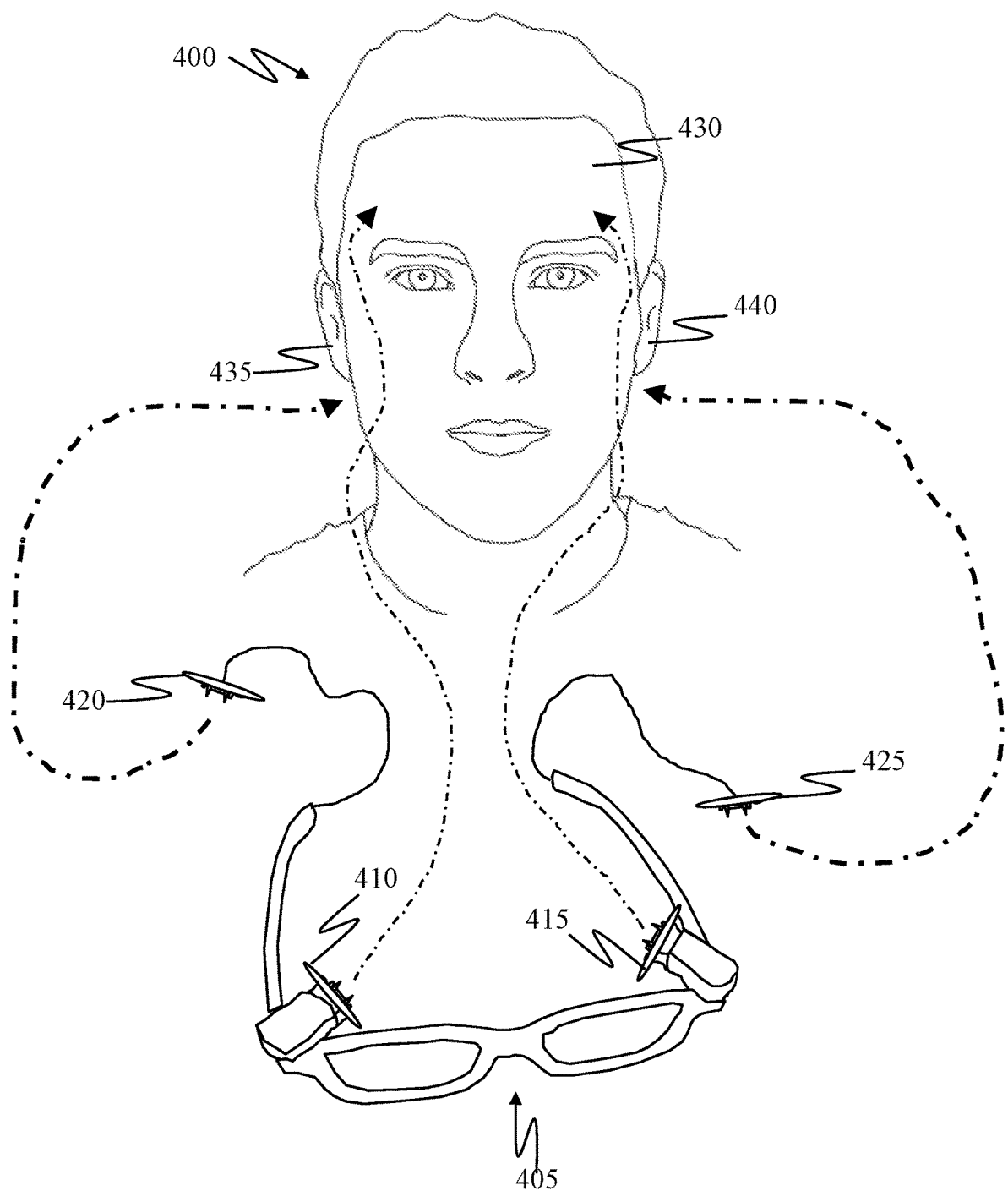
FIG. 4. Picture depicting one embodiment of a GVS system comprising electrodes and modified eyewear worn by a subject.

FIG. 4 is a picture depicting one embodiment of a GVS system comprising electrodes and modified eyewear, as well as the desired placement of the modified eyewear on a subject for one exemplary embodiment. A subject 400 dons an HID 405 that is in the form of modified eyeglasses comprising electrodes including a left forehead electrode 415, a right forehead electrode 410, a left ear electrode 425 and a right ear electrode 420. As the modified eyewear HID 405 is put into place on the subject's 400 head, the forehead electrodes 410, 415 come into contact with the subject's 400 forehead 430. Preferably, the forehead electrodes 410, 415 are adapted to be adjustable such that the modified eyewear HID 405 can be worn comfortably by any subject 400 and the forehead electrodes 410, 415 adjust in and out to place sufficient pressure against the subject's 400 forehead 430 without causing discomfort or pain. Preferably once the modified eyewear HID 405 is in place on the subject's 400 head, the ear electrodes 420, 425 are put into place near the subject's ear's 435, 440. Once the modified eyewear HID 405 is donned and the forehead electrodes 410, 415 are suitably situated against the subject's 400 forehead 430, the left ear electrode 425 can be attached or affixed into place near the subject's left ear 440, and the right ear electrode 420 can be attached or affixed into place near the subject's right ear 435, each in a location suited for interaction with the subject's 400 vestibular system. The ear electrodes 420, 425 may be tethered to the modified eyewear HID 405, as in the depicted embodiment, such that the electrodes are in wired communication with the electronic components of the modified eyewear HID 405. Alternatively, the ear electrodes 420, 425 may be wirelessly connected, and thus in wireless communication with, the modified eyewear HID 405 and/or other electronic component(s), each of which would then require suitable wireless communication hardware incorporated into each component, preferably for two-way wireless communication. The ear electrodes 420, 425 are preferably attached or affixed to the subject in a comfortable and secure yet easily removable manner. One example of an ear electrode attachment system might include an adhesive patch or garment that is adhered to the subject's skin covering the ear electrodes 420, 425. Preferably, the ear electrodes 420, 425 (as well as the forehead electrodes 410, 415) have one or more surface features (not labeled) that help anchor and secure the electrodes to the subject's skin, as well as facilitate the acquisition of physiological signals from the subject and the delivery of stimulation to the subject.

Figure 5:
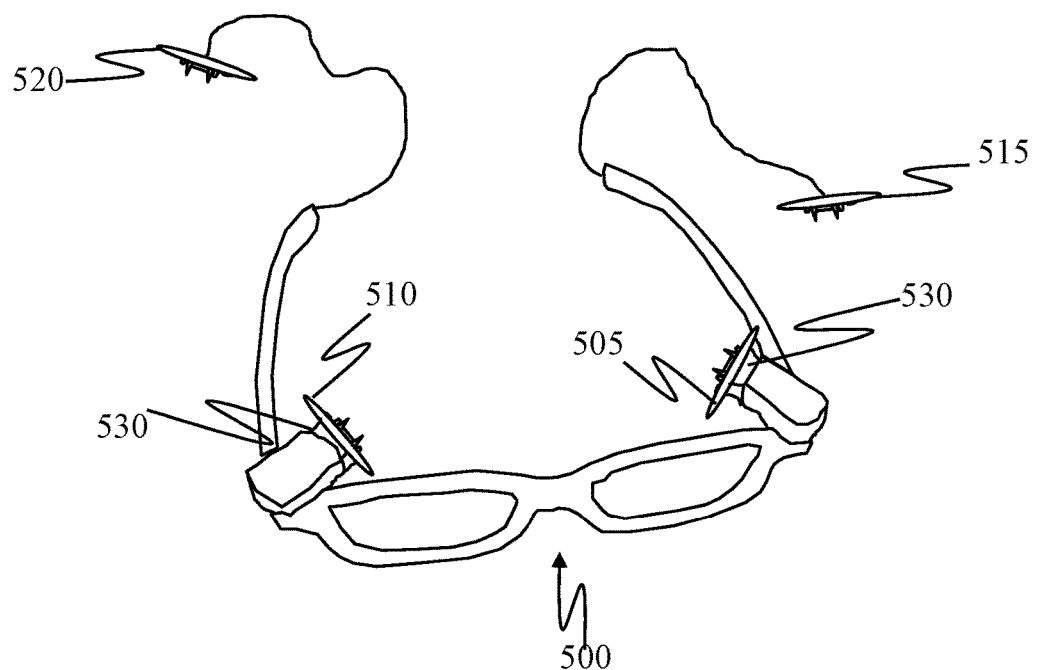
FIG. 5. Picture depicting one embodiment of a GVS system comprising electrodes and modified eyewear.

FIG. 5 is a picture depicting one embodiment of a GVS system comprising electrodes and modified eyewear. The picture depicts an HID 500 in the form of modified eyeglasses comprising electrodes including a left forehead electrode 505, a right forehead electrode 510, a left ear electrode 515 and a right ear electrode 520. As the modified eyewear HID 500 is put into place on the subject's head (not shown), the forehead electrodes 505, 510 come into contact with the subject's forehead. Preferably, the forehead electrodes 505, 510 are adapted to be adjustable such that the modified eyewear HID 500 can be worn comfortably by any subject and the forehead electrodes 505, 510 adjust in and out to place sufficient pressure against the subject's forehead without causing discomfort or pain. The forehead electrode 505, 510 mounts 525, 530 preferably comprise adjustable components such that the electrodes 505, 510 can move with the modified eyewear HIG 500 and the subject's forehead to maintain substantially constant and secure pressure holding the electrodes 505, 510 against the subject's forehead. Further preferably, the mounts 525, 530 adjust to maintain substantially constant pressure to avoid slippage or moving of the electrodes 505, 510 on the subject's forehead. Still further preferably, the mounts 525, 530 preferably are continuously adjustable such that the mounts allow the electrodes 505, 510 to move and adjust continuously and in real-time with the movement of the subject and/or the modified eyewear HID 500 while worn by the subject to maintain such pressure substantially continuously. Preferably once the modified eyewear HID 500 is in place on the subject's head, the ear electrodes 515, 520 are put into place near the subject's ears. The ear electrodes 515, 520 may be tethered to the modified eyewear HID 500, as in the depicted embodiment, such that the electrodes are in wired communication with the electronic components of the modified eyewear HID 500. Alternatively, the ear electrodes 515, 520 may be wirelessly connected, and thus in wireless communication with, the modified eyewear HID 500 and/or other electronic component(s), each of which would then require suitable wireless communication hardware incorporated into each component, preferably for two-way wireless communication. Preferably, the forehead electrodes 505, 510 and the ear electrodes 515, 520 have one or more surface features (not labeled) that help anchor and secure the electrodes to the subject's skin, as well as facilitate the acquisition of physiological signals from the subject and the delivery of stimulation to the subject.

Figures 6A, 6B:
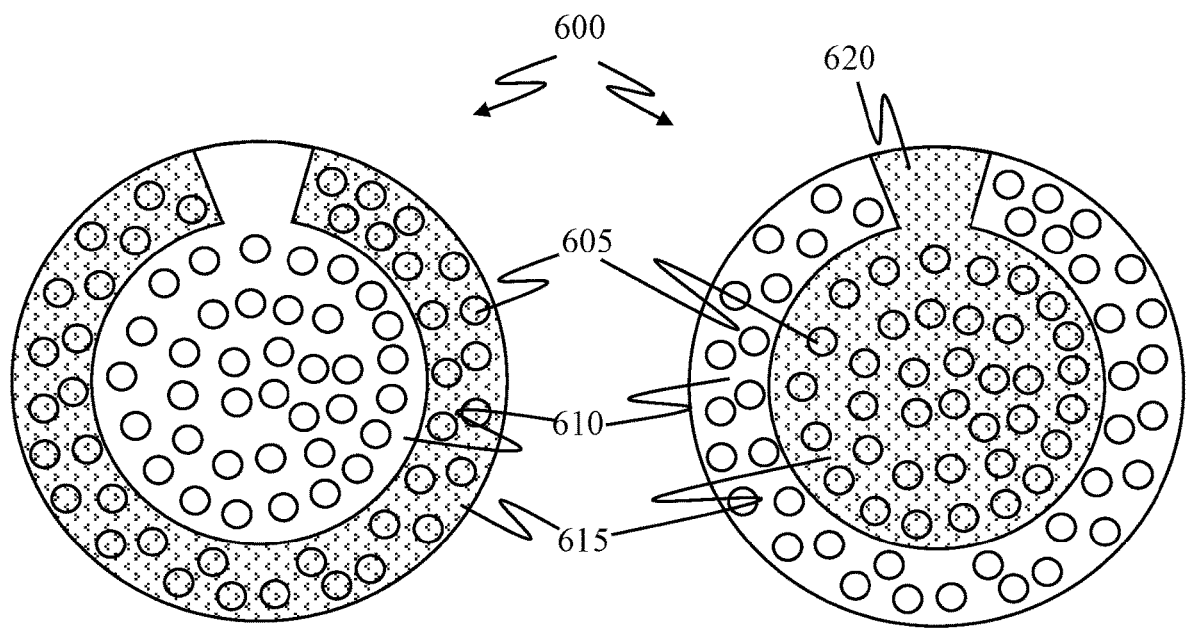
FIGS. 6A-B. Diagrams depicting various embodiments of dual-mode electrodes of the present invention that simultaneously measure and acquire signals from the subject and provide or inject stimulation to the subject.

FIGS. 6A and 6B depict two alternative embodiments of dual-mode electrodes adapted to simultaneously measure or acquire signals from a subject and provide electrical stimulation to the subject. More specifically, the present figures depict the lower surface of two embodiments of dual-mode electrodes. Each embodiment comprises a plurality of surface features 605, a stimulating region 610 and a sensing region 615. FIG. 6A depicts an embodiment wherein the sensing region 615 constitutes a majority of the outer portion of the lower surface of the electrode, while the stimulation region 610 substantially constitutes the center region of the lower surface of the electrode and optionally a portion of the outer region thereof. Conversely, FIG. 6B depicts an embodiment wherein the stimulation region 610 constitutes a majority of the outer portion of the lower surface of the electrode, while the sensing region 615 substantially constitutes the center region of the lower surface of the electrode and a portion of the outer region thereof. In both embodiments, the sensing region 615 is optionally coated in a conductive compound or coating (indicated by the pattern-filled regions). The conductive compound or coating helps facilitate measurement and/or acquisition of signals from the subject's body and provides a cleaner, sharper signal the requires less processing and modification prior to analysis. The stimulation region 610 is preferably not coated in the conductive compound or coating (indicated by the absence of pattern-filling) because such compound or coating may increase the likelihood and/or severity of dermal effects on the subject's skin as electrical stimulation is applied thereto. In the embodiment depicted in FIG. 6B, the sensing region 615 with the conductive compound or coating optionally extends from the center region of the lower surface of the electrode 600 to the edge, and up and over the upper surface (not shown) to a connector (not shown). The conductive compound or coating extending to the connector maintains a low-impedance pathway 620 from the sensing region 615 to the connector not shown) thus allowing acquired signals to be more readily and accurately transmitted to the electronic components for analysis. The conductive compound or coating may cover the entire sensing region 615, and the pathway 620 to the upper surface (not shown) of the electrode 600, or merely a portion or specific patter thereof, and the particular coating adaptation depends on the type and style of electrode 600 used, and the application. The importance of the conductive compound or coating, and a more detailed description of the various methods and adaptations of the coating process for electrodes is described in greater detail in U.S. Pat. No. 9,193,313, herein incorporated by reference. The surface features 605 are preferably comprised on both the sensing region 615 and the stimulation region 610, though may be optionally absent from either region depending on the embodiment. With respect to the sensing region 615, the surface features 605 help to perturb the outer layers of the skin and to facilitate acquisition and/or measurement of physiological signals from the lower layers thereof. With respect to the stimulation region 610, the surface features 605 help to increase the surface area of the stimulation region and also to help direct the stimulation in order to help minimize dermal effects and irritation on the subject's skin.

Figure 7A:
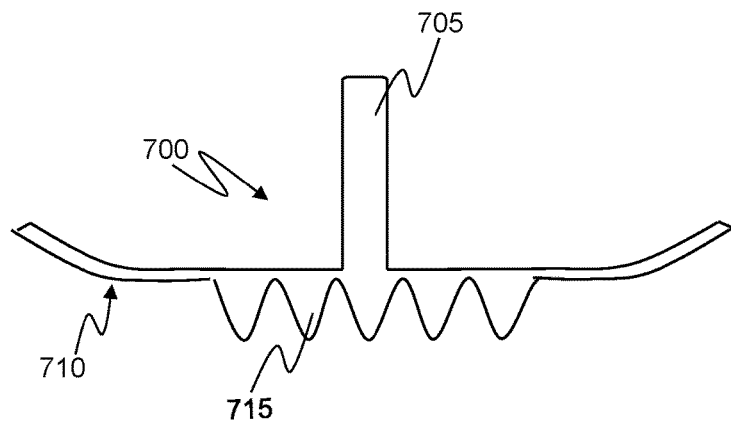
FIGS. 7A-B. Pictures depicting alternative electrode embodiments for use with various embodiments of the present invention.
Figure 7B:
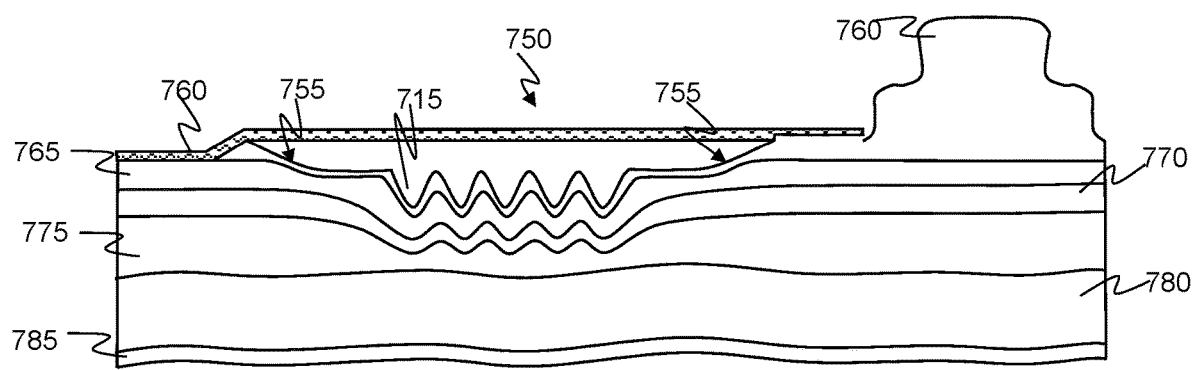

FIGS. 7A and 7B depict various alternative embodiments of electrodes for use in conjunction with the present invention. FIG. 7A illustrates a cross-section of an embodiment of an electrode comprising a metal electrode 700. In the depicted embodiment of a stamped metal electrode 700, the body of the electrode 700 is constructed or manufactured from a conductive metal, and is preferably a unitary construction whereby the entire electrode is formed from one piece of metal, for example via a stamping process or other such process known in the art as being able to form such shapes and devices from a single piece of metal with solid construction. The depicted metal electrode 700 comprises a connector 705, an encouragement lip 710, and surface features 102 on the lower surface of the electrode 700. Although not shown, a conductive coating and/or ionic compound may be applied to all or a portion of the lower surface of the electrode 700 in order to facilitate measurement and acquisition of physiological and/or electrophysiological signals from the subject. Preferably, if a conductive coating and/or ionic compound is used, it is placed on only a portion of the lower surface, such as for example, just the tips of the surface features 715. This configuration minimizes the amount of the expensive coating and/or ionic compound required, and thus minimizes the cost of the electrode 700, while still providing the coating to facilitate the transmission of biopotentials or physiological signals from the subject, through the conductive electrode. The conductive metal body of the device then provides an electrical pathway by which those signals may be transmitted. The encouragement lip 710 is adapted for helping the electrode 700 remain in stable, secure contact with a subject's skin by stabilizing and helping to situate or force the surface features of the device against the subject's skin, and is described in greater detail in U.S. Pat. No. 9,193,313, herein incorporated by reference.

FIG. 7B illustrates a cross-section of another embodiment of a metal electrode in place on a subject's skin, with the surface features portrayed in the act of depressing, and thus displacing, cracking, or perturbing the subject's skin, without actually penetrating through the outermost layer(s). In this embodiment, and adhesive layer 760 holds the electrode 750 to the stratum corneum 765, and the encouragement lip 755 and surface features 715 merely depress, and thus displace, crack, or perturb the stratum corneum 765. The stratum lucidum 770, stratum granulosum 775, stratum spinosum 780, and stratum basale 785, show similar perturbations; however, with decreasing severity as distance from the stratum corneum 765 increases. Optionally, a conductive coating and/or ionic compound (not shown) may be included on the device, or more preferably just on the surface features 715, or just the tips or ends of the surface features 715, as described with respect to FIG. 7A. As noted, the surface features 715 may pierce or break at least the stratum corneum, though such piercing may not be desirable and mere perturbation of these outer, high impedance layers may be preferred. Preferably, the entire electrode 750 in the depicted embodiment 360 is made from metal that is strong enough to resist a change in shape by forces exerted by a subject's skin as surface features 715 of the electrode displace, crack, or perturb the skin and are held in place by the adhesive collar 760. Additionally, the metal should be electrically conductive so as to allow monitoring equipment (not shown) connected to the electrode 750 via the connector 760 to measure and/or acquire biopotentials from the subject. The location of the connector 760 offset from above the surface features 715 and encouragement lip 755, rather than above them, facilitates the stamped metal manufacturing process as well as provides for strain relief for the surface features 715 from any lead connector (not shown) attached to the connector 760. As the weight from a lead connector attached to the connector 760 pulls on the connector, it will not provide the direct force away from the surface of the skin as would normally occur in an embodiment where the connector is directly above and in-line with the surface of the device in contact with the subject's skin. Instead, the offset connector 760 disperses some of the forces pulling the device away from the surface of the skin, and provides a degree of strain relief which helps the device remain more securely attached to the subject for a longer period of time. Further, all or a portion, for example just the tips or ends of the surface features 715 may be covered in conductive coating and/or ionic compound (not shown). This coating or compound creates a redox reaction which helps reduce the electrical impedance and drive the transmission of biopotentials or physiological signals from the subject to monitoring equipment (not shown), thus causing the measurement or acquisition of physiological and/or electrophysiological signals to be more accurate.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed:

1. A method of providing galvanic vestibular stimulation (GVS) to a subject to provide perceived motion, the method comprising steps of:
providing to the subject a GVS system comprising a human interface device (HID), a central control device (CCD) and a current application device (CAD), the HID comprising at least one electrophysiological sensor and at least four electrodes, the at least one electrophysiological sensor and each electrode comprising an upper surface and a lower surface with a plurality of protruding surface features disposed on the lower surface, the CCD comprising a processor comprising at least one algorithm, and the CAD comprising a processor and an electrical current generator;
integrating and synchronizing, with the CCD processor and at least one algorithm, input data to generate a GVS profile, the input data comprising at least in part electrophysiological data from the at least one electrophysiological sensor,
translating the GVS profile, with the CAD processor into a current application profile;
generating with the CAD electrical current generator a stimulation current according to the determined current application profile; and
providing the generated stimulation current to the subject with at least two of the electrodes to provide a perceived motion to the subject in at least one dimension or direction.

2. The method of claim 1, wherein at least two of the electrodes are forehead electrodes and at least two electrodes are ear electrodes, and the HID is adapted to be a modified eyewear or eyeglasses apparatus adapted to position the electrodes on the subject's head in their respective locations.

3. The method of claim 2, wherein at least two of the electrodes are dual-mode electrodes adapted to simultaneously acquire signals from the subject and provide electrical stimulation to the subject, and the at least two dual-mode electrodes comprise the at least one electrophysiological sensor without requiring a separate or additional electrophysiological sensor.

4. The method of claim 2, wherein at least two of the electrodes comprise a flexible substrate adapted to conform to skin topography of the subject to increase surface area contact of the electrode with the subject's skin.

5. The method of claim 3, further comprising a self-adjustment step in which the user selects a pre-programmed GVS profile based on an activity or instance of use of the GVS system.

6. The method of claim 5, further comprising at least one sensor adapted to measure movement or orientation of the subject, and the input data comprises movement or orientation data from the at least one sensor adapted to measure movement or orientation in addition to the electrophysiological data from the at least one electrophysiological sensor.

7. The method of claim 3, wherein the dual-mode electrodes each comprise a sensing region and a stimulation region, and the sensing region is at least partially coated in a conductive coating but the stimulation region has no such coating.

8. A method of providing galvanic vestibular stimulation (GVS) to a subject to provide perceived motion, the method comprising steps of:
providing to the subject a GVS system comprising a human interface device (HID), a central control device (CCD) and a current application device (CAD), the HID comprising at least one electrophysiological sensor and a modified eyewear or eyeglasses apparatus with at least two forehead electrodes and at least two ear electrodes, the at least one electrophysiological sensor and each electrode comprising an upper surface and a lower surface with a plurality of protruding surface features disposed on the lower surface, the CCD comprising a processor comprising at least one algorithm, and the CAD comprising a processor and an electrical current generator;
integrating and synchronizing, with the CCD processor and at least one algorithm, input data to generate a GVS profile, the input data comprising at least in part electrophysiological data from the at least one electrophysiological sensor,
translating the GVS profile, with the CAD processor into a current application profile;
generating with the CAD electrical current generator a stimulation current according to the determined current application profile; and
providing the generated stimulation current to the subject with at least two of the electrodes to provide a perceived motion to the subject in at least one dimension or direction.

9. The method of claim 8, wherein at least two of the electrodes are dual-mode electrodes adapted to simultaneously acquire signals from the subject and provide electrical stimulation to the subject, and the at least two dual-mode electrodes comprise the at least one electrophysiological sensor without requiring a separate or additional electrophysiological sensor.

10. The method of claim 8, wherein at least two of the electrodes comprise a flexible substrate adapted to conform to skin topography of the subject to increase surface area contact of the electrode with the subject's skin.

11. The method of claim 9, further comprising a self-adjustment step in which the user selects a pre-programmed GVS profile based on an activity or instance of use of the GVS system.

12. The method of claim 11, further comprising at least one sensor adapted to measure movement or orientation of the subject, and the input data comprises movement or orientation data from the at least one sensor adapted to measure movement or orientation in addition to the electrophysiological data from the at least one electrophysiological sensor.

13. The method of claim 9, wherein the dual-mode electrodes each comprise a sensing region and a stimulation region, and the sensing region is at least partially coated in a conductive coating but the stimulation region has no such coating.

14. A method of providing galvanic vestibular stimulation (GVS) to a subject to provide perceived motion, the method comprising steps of:
provinding to the subject a GVS system comprising a human interface device (HID), a central control device (CCD) and a current application device (CAD), the HID comprising at least one electrophysiological sensor and a modified eyewear or eyeglasses apparatus with at least two dry forehead electrodes and at least two dry ear electrodes, the at least one electrophysiological sensor and each electrode comprising an upper surface and a lower surface with a plurality of protruding surface features disposed on the lower surface, the CCD comprising a processor comprising at least one algorithm, and the CAD comprising a processor and an electrical current generator;
integrating and synchronizing, with the CCD processor and at least one algorithm, input data to generate a GVS profile, the input data comprising at least in part electrophysiological data from the at least one electrophysiological sensor,
translating the GVS profile, with the CAD processor into a current application profile;
generating with the CAD electrical current generator a stimulation current according to the determined current application profile; and
providing the generated stimulation current to the subject with at least two of the electrodes to provide a perceived motion to the subject in at least one dimension or direction.

15. The method of claim 14, wherein at least two of the electrodes are dual-mode electrodes adapted to simultaneously acquire signals from the subject and provide electrical stimulation to the subject, and the at least two dual-mode electrodes comprise the at least one electrophysiological sensor without requiring a separate or additional electrophysiological sensor.

16. The method of claim 14, wherein at least two of the electrodes comprise a flexible substrate adapted to conform to skin topography of the subject to increase surface area contact of the electrode with the subject's skin.

17. The method of claim 15, further comprising a self-adjustment step in which the user selects a pre-programmed GVS profile based on an activity or instance of use of the GVS system.

18. The method of claim 17, further comprising at least one sensor adapted to measure movement or orientation of the subject, and the input data comprises movement or orientation data from the at least one sensor adapted to measure movement or orientation in addition to the electrophysiological data from the at least one electrophysiological sensor.

19. The method of claim 15, wherein the dual-mode electrodes each comprise a sensing region and a stimulation region, and the sensing region is at least partially coated in a conductive coating but the stimulation region has no such coating.

20. The method of claim 15, wherein the current application profile is further based on the constraint of minimizing dermal effects on the subject's skin.

* * * * *